(12) United States Patent
Yamada et al.

(10) Patent No.: US 10,060,452 B2
(45) Date of Patent: Aug. 28, 2018

(54) PYROTECHNIC ACTUATOR MECHANISM, SYRINGE AND IGNITER ASSEMBLY

(71) Applicant: DAICEL CORPORATION, Osaka (JP)

(72) Inventors: Ryohei Yamada, Prachinburi (TH); Takaya Masumoto, Hyogo (JP)

(73) Assignee: DAICEL CORPORATION, Osaka (JP)

( * ) Notice: Subject to any disclaimer, the term of this patent is extended or adjusted under 35 U.S.C. 154(b) by 0 days.

(21) Appl. No.: 15/679,080

(22) Filed: Aug. 16, 2017

(65) Prior Publication Data
US 2017/0343021 A1 Nov. 30, 2017

Related U.S. Application Data

(63) Continuation of application No. PCT/JP2016/054481, filed on Feb. 16, 2016.

(30) Foreign Application Priority Data

Feb. 17, 2015 (JP) .................................. 2015-029074

(51) Int. Cl.
*F15B 15/19* (2006.01)
*F42B 3/04* (2006.01)
(Continued)

(52) U.S. Cl.
CPC ................ *F15B 15/19* (2013.01); *F42B 3/04* (2013.01); *F42B 3/12* (2013.01); *A61M 5/30* (2013.01)

(58) Field of Classification Search
CPC .... F15B 15/19; F42B 3/04; F42B 3/10; F42B 3/12; F42B 3/103; F42B 3/125; A61M 5/30

(Continued)

(56) References Cited

U.S. PATENT DOCUMENTS 3,106,131 A * 10/1963 Barr ........................ F15B 15/19
102/531
3,404,598 A * 10/1968 Angelos .................. F42B 3/006
102/530

(Continued)

FOREIGN PATENT DOCUMENTS

| JP | S59-107979 U | 6/1984 |
| JP | 2006-256396 A | 9/2006 |
| JP | 2009-061803 A | 3/2009 |

OTHER PUBLICATIONS

International Search Report issued in related application PCT/JP2016/054481 dated May 24, 2016.

(Continued)

*Primary Examiner* — James S Bergin
(74) *Attorney, Agent, or Firm* — Knobbe Martens Olson & Bear LLP (57) ABSTRACT

A pyrotechnic actuator mechanism comprises a cover member which includes a first wall member which is opposed to a release portion of an ignition unit, and a second wall member which is connected thereto and which has a free end portion embedded in a fixing member. When an ignition charge contained in the ignition unit is combusted, then the cover member is moved in the propulsion direction so that a predetermined closed space is expanded in the propulsion direction of a piston, and the movement of the cover member is regulated so that a state, in which the free end portion of the second wall member is embedded in the fixing member, is maintained at a maximum propulsion position of the cover member. Accordingly, the residue, which is produced by the combustion of the ignition charge, is preferably suppressed from being discharged or emitted to the outside.

15 Claims, 7 Drawing Sheets

(51) Int. Cl.
*F42B 3/12* (2006.01)
*A61M 5/30* (2006.01)

(58) Field of Classification Search
USPC ........ 102/202.5, 202.9, 202.12, 202.14, 530, 102/531; 604/68, 39, 70, 143
See application file for complete search history.

(56) References Cited

U.S. PATENT DOCUMENTS

| | | | | |
|---|---|---|---|---|
| 4,091,621 | A * | 5/1978 | Patrichi | F15B 15/19 |
| | | | | 60/635 |
| 4,860,698 | A * | 8/1989 | Patrichi | F42B 3/006 |
| | | | | 123/24 R |
| 6,758,829 | B2 * | 7/2004 | Alexandre | A61M 5/30 |
| | | | | 604/68 |
| 6,851,372 | B2 * | 2/2005 | Bender | F15B 15/261 |
| | | | | 102/202.14 |
| 6,942,261 | B2 * | 9/2005 | Larsen | B60R 19/32 |
| | | | | 180/274 |
| 7,063,019 | B2 | 6/2006 | Parks et al. | |
| 7,455,655 | B2 | 11/2008 | Alexandre et al. | |
| 7,698,895 | B2 * | 4/2010 | Bretfeld | F15B 15/19 |
| | | | | 60/632 |
| 8,596,179 | B2 * | 12/2013 | Enzmann | B29C 45/14311 |
| | | | | 137/68.13 |
| 2006/0218918 | A1 | 10/2006 | Hirooka et al. | |

OTHER PUBLICATIONS

International Preliminary Report on Patentability (English translation) dated Aug. 22, 2017 in International Application No. PCT/JP2016/054481, filed Feb. 16, 2016.

\* cited by examiner

PYROTECHNIC ACTUATOR MECHANISM, SYRINGE AND IGNITER ASSEMBLY

CROSS-REFERENCE TO RELATED APPLICATIONS

This application is a continuation application, and claims the benefit under 35 U.S.C. §§ 120 and 365 of PCT Application No. PCT/JP2016/054481, filed on Feb. 16, 2016, which is hereby incorporated by reference. PCT/JP2016/054481 also claimed priority from Japanese Patent Application No. 2015-029074 filed on Feb. 17, 2015, the entire contents of which are incorporated by reference.

TECHNICAL FIELD

The present disclosure relates to a pyrotechnic actuator mechanism which obtains an output by means of the combustion of an ignition charge, a syringe which utilizes the same, and an igniter assembly which is usable in order to ignite or inflame the ignition charge.

BACKGROUND ART

A pyrotechnic actuator mechanism, which is an actuator mechanism to obtain an output by moving a piston by means of the force of an ignition charge, is used for apparatuses including, for example, an airbag system for vehicles, a pedestrian protection system, a current breaker, a perforator, and a fire extinguishing system. Further, a syringe, which discharges or injects an injection objective substance by means of a pressurized piston, is also known in the field of medical treatment. A pyrotechnic actuator mechanism is widely investigated as a driving source for the syringe as described above. For example, Patent Literature 1 discloses an actuator mechanism which obtains a predetermined output by developing a bellows cup which is expandable as shown in FIG. 1 or a bendable/stretchable cup which is shown in FIG. 6, by means of a combustion product produced by the combustion of an ignition charge.

In the case of the pyrotechnic actuator mechanism as described above, the ignition charge is used as the driving source for the piston. Therefore, any residue is produced to no small extent upon the combustion of the ignition charge. Then, even when the produced residue is in a small amount, it is preferable that the residue is not discharged or emitted to the outside of the actuator mechanism. For example, in the case of a pyrotechnic actuator mechanism shown in Patent Literature 2, a sack (see FIG. 6A), which has been folded up from the beginning, is expanded (see FIG. 6B) by a combustion product produced by the combustion of an ignition charge, and thus an output is obtained for an actuator. In this situation, the combustion product is in a state of being sealed by the sack. Therefore, the combustion product, which contains the residue, hardly leaks out to the outside.

Further, in the case of a pyrotechnic actuator mechanism shown in Patent Literature 3, such a structure is adopted that a piston is extruded by raising the pressure of a gas chamber in accordance with an operation of a gas generator provided on one end side of a cylinder. The movement of the piston is continued until the piston collides with a bush provided in the cylinder. In this case, the clearance is extremely decreased for the cylinder and a main body unit of the piston. However, the combustion residue is not completely prevented from being discharged or emitted to the outside of the cylinder.

PRIOR ART LITERATURES

Patent Literatures

Patent Literature 1: U.S. Pat. No. 7,063,019
Patent Literature 2: U.S. Pat. No. 7,455,655
Patent Literature 3: Japanese Patent Application Laid-Open No. 2009-61803

SUMMARY

Problems to be Solved

In the case of the pyrotechnic actuator mechanism, the output is obtained by utilizing the energy obtained by the combustion of the ignition charge. Therefore, the output can be made relatively large, while providing a relatively small structure of the actuator mechanism. It is possible to say that the pyrotechnic actuator mechanism is a useful actuator mechanism in which the output efficiency is extremely satisfactory. However, the residue is produced when the ignition charge is combusted. Therefore, it is preferable that the residue does not leak out to the outside, in view of the hygiene and in view of the influence exerted, for example, on mechanical parts disposed around the actuator mechanism.

However, if it is intended to seal the combustion product of the ignition charge in the certain space by means of the bag such as the sack or the like as mentioned in Patent Literature 1 and Patent Literature 2 described above, the relatively large pressure is easily exerted by the high combustion energy and the contained combustion residue. On the other hand, when the sealed space is formed by bending the member such as the bellows cup as mentioned in Patent Literature 1, the pressure is easily concentrated at the bent portion. Therefore, it is possible to find out any scope for improvement in view of the strength of the sealed space. Further, it is impossible to sufficiently suppress the discharge or emission of the residue to the outside by merely adjusting the clearance as mentioned in Patent Literature 3.

Accordingly, in view of the problems described above, an object of the present disclosure is to provide a technique which preferably suppresses the discharge or emission of the residue produced by the combustion of the ignition charge to the outside.

Means for Solving the Problems

In order to solve the problems described above, according to the present disclosure, a cover member which covers an ignition unit including an ignition charge is provided in a pyrotechnic actuator mechanism. Specifically, the present disclosure resides in a pyrotechnic actuator mechanism which has an ignition unit including an ignition charge to be ignited or inflamed by an ignition current supplied from outside and which includes a piston constructed to be driven and propelled in a propulsion hole provided in a housing in accordance with combustion energy of the ignition charge; the pyrotechnic actuator mechanism comprising a cover member which covers a predetermined portion of the ignition unit including at least a release portion for releasing, from the ignition unit, a combustion product produced by combustion of the ignition charge in the ignition unit, which is formed to define a predetermined closed space between the cover member and the ignition unit, and which is arranged to transmit the combustion energy of the ignition charge to the piston; and a fixing member which fixes the ignition unit before and after the combustion of the ignition charge. Then, the cover member includes a first wall member which is a wall member for defining the predetermined closed space, which is opposed to the predetermined portion of the ignition unit, and which is brought in contact with the piston; and a second wall member which is a wall member connected to the first wall member, for defining the predetermined closed space, which extends in the propulsion direction of the piston, and which has a free end portion disposed on a side opposite to a connecting end portion with respect to the first wall member, the free end portion being embedded in the fixing member. Further, the cover member is moved in the propulsion direction so that the predetermined closed space is expanded in the propulsion direction of the piston when the ignition charge is combusted, and the movement of the cover member in the propulsion direction is regulated so that a state, in which the free end portion of the second wall member is embedded in the fixing member, is maintained at a maximum propulsion position of the cover member.

The pyrotechnic actuator mechanism according to the present disclosure uses the ignition charge as the output source for the actuator. The ignition charge is exemplified, for example, by ZPP (mixture of zirconium and potassium perchlorate) and black powder (for example, boron saltpeter). Then, the ignition unit, which includes the ignition charge, is covered by the cover member, and thus the combustion product of the ignition charge is sealed in the predetermined closed space defined between the cover member and the ignition unit. Note that it is not necessarily indispensable that the cover member should cover the entire ignition unit. It is enough that the cover member is arranged with respect to the ignition unit so that the cover member covers at least the predetermined portion at which the combustion product is released. That is, it is appropriate that the cover or covering is formed for the ignition unit by the cover member in view of the suppression of the discharge or emission of the combustion product or the ignition charge to the outside. Note that it is enough that the housing forms the propulsion hole in which the piston is driven and propelled. The housing may be an outer shell container itself of the actuator mechanism itself or any other part arranged in an outer hull container.

Then, the cover member is the member which is provided to transmit the combustion energy of the ignition charge to the piston so that the piston is driven and propelled. The cover member has the first wall member and the second wall member for defining the predetermined closed space described above. The first wall member is the wall member which is opposed to the predetermined portion for releasing the combustion product of the ignition charge and which is arranged to be brought in contact with the piston. On this account, the first wall member is constructed to receive the pressure from the combustion product, i.e., the combustion energy generated by the combustion of the ignition charge to a relatively great extent. As a result, the first wall member receives the force to make separation from the ignition unit. The force is transmitted to the piston brought in contact therewith. Therefore, the direction of separation is the propulsion direction of the piston. Note that as for the contact between the first wall member and the piston, the first wall member and the piston may be arranged in a contact state in the uncombusted state of the ignition charge. In another method, the both may be arranged to be brought in contact with each other after the combustion, even when the both are not brought in contact in the uncombusted state.

On the other hand, the second wall member is the wall member which is connected to the first wall member. Therefore, when the first wall member receives the force in accordance with the combustion of the ignition charge as described above, the second wall member is also moved in accordance therewith in the direction in which the first wall member is separated from the ignition unit. In this situation, the free end portion of the second wall member is in the state of being embedded in the fixing member. However, the free end portion is not consequently in a state in which the free end portion is fixed by the fixing member. Therefore, the separation from the ignition unit is not inhibited when the ignition charge is combusted. In other words, the free end portion of the second wall member is fixed to such an extent that the free end portion can be moved by receiving the combustion energy of the ignition charge. On the other hand, the free end portion of the second wall member is embedded in the fixing member, and thus the hermetic sealing performance of the predetermined closed space described above, i.e., the ability to suppress the discharge or emission of the combustion product of the ignition charge is secured or guaranteed.

Then, when the ignition charge is combusted, the first wall member is principally pressurized by the combustion product as described above. Accordingly, the cover member is moved in the propulsion direction of the piston, and the predetermined closed space is progressively expanded in the propulsion direction. In accordance with the movement of the cover member, the combustion energy of the ignition charge is preferably transmitted to the piston by the aid of the cover member. Further, the state, in which the free end portion of the second wall member is embedded in the fixing member, is maintained during the movement of the cover member, i.e., during the period until the cover member arrives at the maximum propulsion position after the start of the movement. Therefore, the hermetic sealing performance of the predetermined closed space is always maintained in the period of movement of the cover member.

In this way, in the pyrotechnic actuator mechanism according to the present disclosure, both of the maintenance of the predetermined closed space for sealing the combustion product of the ignition charge and the efficient transmission of the combustion energy to the piston are fulfilled. As a result, the discharge or emission of the residue contained in the combustion product to the outside is preferably suppressed without decreasing the output efficiency of the pyrotechnic actuator. Note that the cover member receives the combustion energy, and hence the cover member is preferably made of metal having a high thermal strength. Further, it is preferable that any fragile portion or the like, on which the pressure is concentrated, is not formed so that the predetermined closed space is maintained before and after the combustion of the ignition charge as well.

In this context, in the pyrotechnic actuator mechanism described above, an embedded state of the free end portion in the fixing member may be maintained by means of such an arrangement that an embedding distance of the second wall member in the fixing member in an uncombusted state of the ignition charge, i.e., an embedding depth is longer than a movement distance of the cover member in the propulsion direction at a maximum propulsion position of the cover member. When the arrangement as described above is adopted, the hermetic sealing performance of the predetermined closed space is thereby preferably maintained during the period of movement of the cover member caused by the combustion of the ignition charge.

Further, in the pyrotechnic actuator mechanism described above, the cover member may further include a protruding portion which is disposed at a portion of contact with the piston at the first wall member and which protrudes toward the piston. In this case, an outer diameter of the protruding portion is formed to be smaller than an outer diameter of the piston, and an outer diameter of the first wall member is formed to be larger than the outer diameter of the piston. When the outer diameter of the protruding portion is formed to be smaller than the outer diameter of the piston as described above, the protruding portion can thereby enter the propulsion hole of the piston as well. Therefore, the protruding portion enters the propulsion hole during the period until arrival of the cover member at the maximum propulsion position, and thus the distance, by which the cover member can be moved in accordance with the combustion of the ignition charge, can be secured to be longer. It is expected to improve the output of the pyrotechnic actuator mechanism.

Note that the pyrotechnic actuator mechanism may be constructed as follows in relation to the maximum propulsion position of the cover member. That is, the cover member arrives at the maximum propulsion position by bringing the first wall member in contact with an end surface of the housing provided with the propulsion hole and regulating the movement of the cover member in the propulsion direction. The movement of the cover member is regulated by the contact of the first wall member with the end surface of the housing. However, in the contact state, the protruding portion is in a state of entering the propulsion hole of the piston. Therefore, it is expected to improve the output of the pyrotechnic actuator mechanism as described above.

Further, in the pyrotechnic actuator mechanism described above, a gas generating agent, which is combusted by a combustion product of the ignition charge to produce a gas, may be arranged in the protruding portion. The amount of energy applied to the cover member is increased by further arranging the gas generating agent. Therefore, the output of the pyrotechnic actuator mechanism is improved. Note that for example, a nitrocellulose-based generating agent can be utilized as the gas generating agent.

In this context, in the pyrotechnic actuator mechanism described above, the fixing member may include a mold portion which is formed of a resin material and which fixes the ignition unit, and the cover member may be temporarily fixed by the mold portion in a state in which the first wall member is not embedded in the mold portion and in a state in which a wall surface of the second wall member including the free end portion is embedded in the mold portion. Then, the mold portion may fix the ignition unit with respect to an inner wall surface of the housing. When the pyrotechnic actuator mechanism is constructed by adopting the mold portion based on the resin material, it is thereby easy to produce the mechanism. Note that the temporary fixation of the second wall member refers to a state in which the free end portion of the second wall member is fixed to such an extent that the free end portion of the second wall member can be moved in the mold portion, by means of the pressure exerted on the cover member in accordance with the combustion of the ignition charge.

Further, in the form in which the second wall member is embedded in the mold portion, it is preferable that the second wall member is embedded in the mold portion so that the second wall member is in a straight column state along with the propulsion direction in the mold portion. The straight column state is such a state that the outer diameter and the inner diameter of the second wall member are approximately constant in the embedding depth direction in the mold portion. When the second wall member is embedded in the straight column state as described above, the free end portion is easily moved in the mold portion by the pressurizing force upon the combustion of the ignition charge.

Note that the pyrotechnic actuator mechanism described above is applicable to various ways of use, because the residue is not discharged or emitted to the outside, and it is possible to obtain the high output. For example, the pyrotechnic actuator mechanism can be also preferably utilized in the field of medical equipment in which an extremely high hygiene environment is required. For example, the pyrotechnic actuator mechanism can be adopted as an actuator for discharging or injecting an injection objective substance by a syringe. In this case, a syringe can be constructed by the pyrotechnic actuator mechanism as described above, an enclosure in which an injection objective substance to be injected into an injection target area is enclosed, and a nozzle unit which has a flow passage for discharging or injecting the pressurized injection objective substance into the injection target area, the injection objective substance enclosed in the enclosure being pressurized by the aid of the piston driven and propelled by the combustion of the ignition charge in the pyrotechnic actuator. Other than the above, the pyrotechnic actuator mechanism described above may be also preferably adapted, for example, to a current breaker and a perforator.

Further, the present disclosure can be also grasped from an aspect of an igniter for an ignition charge in order to obtain a predetermined output. That is, the present disclosure resides in an igniter assembly comprising an electric ignition igniter which has an ignition unit including an ignition charge; an igniter collar which accommodates the electric ignition igniter; a cover member which covers a predetermined portion of the ignition unit including at least a release portion for releasing, from the ignition unit, a combustion product produced by combustion of the ignition charge in the ignition unit, which is formed to define a predetermined closed space between the cover member and the ignition unit, and which outputs combustion energy of the ignition charge in a predetermined output direction; and a fixing member which fixes the electric ignition igniter unit to the igniter collar before and after the combustion of the ignition charge. Then, the cover member includes a first wall member which is a wall member for defining the predetermined closed space and which is opposed to the predetermined portion of the ignition unit; and a second wall member which is a wall member connected to the first wall member, for defining the predetermined closed space, which extends in the predetermined output direction, and which has a free end portion disposed on a side opposite to a connecting end portion with respect to the first wall member, the free end portion being embedded in the fixing member. Further, the cover member is moved in the predetermined output direction so that the predetermined closed space is expanded in the predetermined output direction when the ignition charge is combusted, and the movement of the cover member in the predetermined output direction is regulated so that a state, in which the free end portion of the second wall member is embedded in the fixing member, is maintained at a maximum propulsion position of the cover member. Accordingly, in relation to the igniter assembly, the output, which is obtained by the combustion, can be improved as far as possible, while preferably suppressing the residue produced by the combustion of the ignition charge from being discharged or emitted to the outside.

Note that the technical concept of the present disclosure, which is disclosed in relation to the pyrotechnic actuator mechanism described above, can be also applied to the igniter assembly provided that any technical inconsistency does not arise. For example, an embedded state of the free end portion in the fixing member may be maintained by means of such an arrangement that an embedding distance of the second wall member in the fixing member in an uncombusted state of the ignition charge is longer than a movement distance of the cover member in the predetermined output direction at a maximum propulsion position of the cover member. Further, the fixing member may include a mold portion which is formed of a resin material and which fixes the electric ignition igniter to the igniter collar; and the cover member may be temporarily fixed by the mold portion in a state in which the first wall member is not embedded in the mold portion and in a state in which a wall surface of the second wall member including the free end portion is embedded in the mold portion. Further, a gas generating agent, which is combusted by a combustion product to generate a gas, may be arranged at a position disposed in the cover member at which the combustion product of the ignition charge can be brought in contact therewith. The ignition unit can include an ignition mechanism such as a bridge wire or the like which is brought in contact with the ignition charge and which is red-heated by the ignition current. No problem arises even when any mechanism other than the bridge wire is adopted as the ignition mechanism.

Further, in the igniter assembly described above, the igniter collar may have a stopper member with which the cover member is brought in contact when the cover member is moved in the predetermined output direction in an igniter accommodating space for accommodating the electric ignition igniter. In this case, when the ignition charge is combusted and the cover member is moved in the predetermined output direction, then the first wall member is brought in contact with the stopper member, the movement of the cover member in the predetermined output direction is regulated, and thus the cover member arrives at the maximum propulsion position. That is, the igniter collar accommodates the electric ignition igniter, while the limit of expansion of the predetermined closed space is determined by the stopper member.

Further, in the igniter assembly described above, the electric ignition igniter may have a header portion which retains the ignition charge; and the cover member may form, on the header portion, an ignition charge accommodating space for accommodating the ignition charge together with the header portion in a state in which the cover member is not fixed to the header portion. That is, the cover member serves for both the definition of the space for accommodating the ignition charge and the definition of the predetermined closed space. Therefore, it is possible to decrease the number of constitutive parts of the igniter assembly.

It is possible to provide the technique which preferably suppresses the discharge or emission of the residue produced by the combustion of the ignition charge to the outside.

EMBODIMENTS

An explanation will be made below with reference to the drawings about an embodiment of the present disclosure. Note that the structure or construction of the following embodiment is described by way of example, and the present disclosure is not limited to the structure or construction of the embodiment.

First Embodiment

<Structure of Pyrotechnic Actuator Mechanism 10>

Figure 1A:
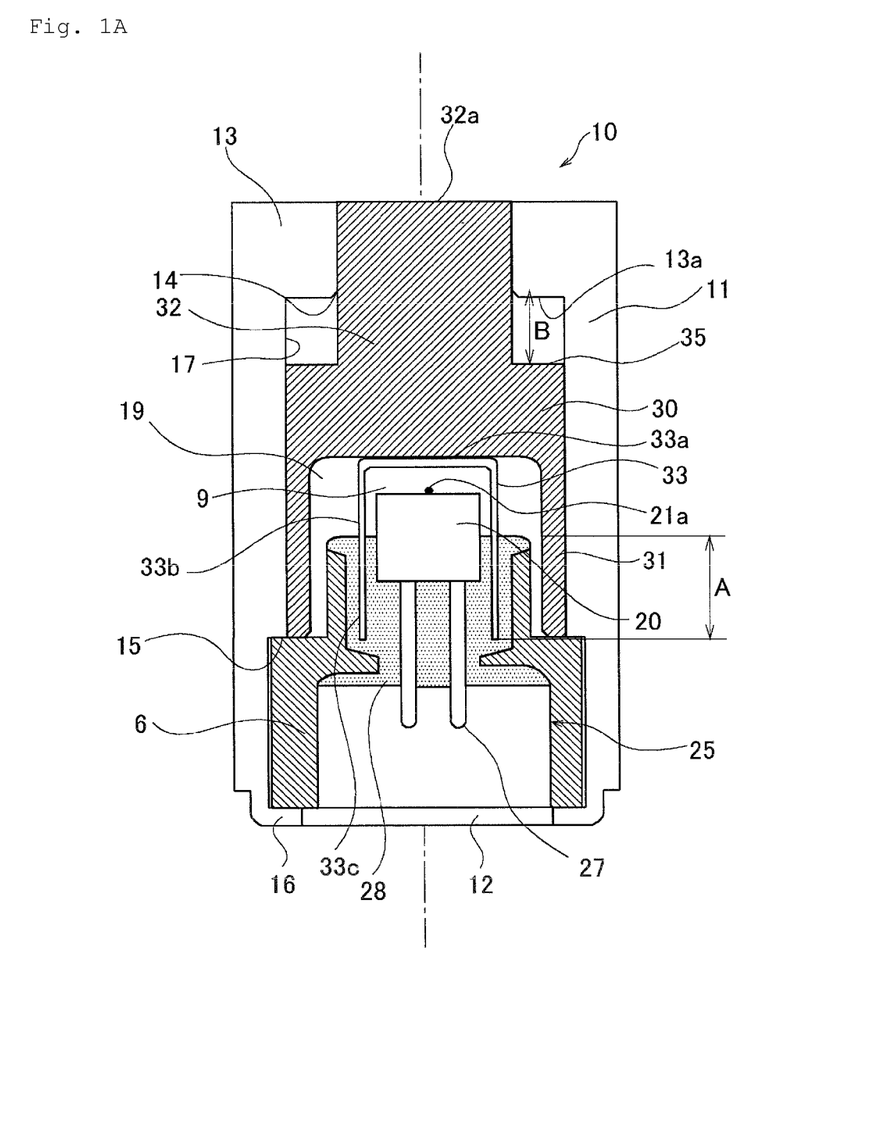
FIG. 1A shows a schematic structure of a pyrotechnic actuator mechanism according to the present disclosure, illustrating a structure brought about before the combustion of an ignition charge.
Figure 1B:
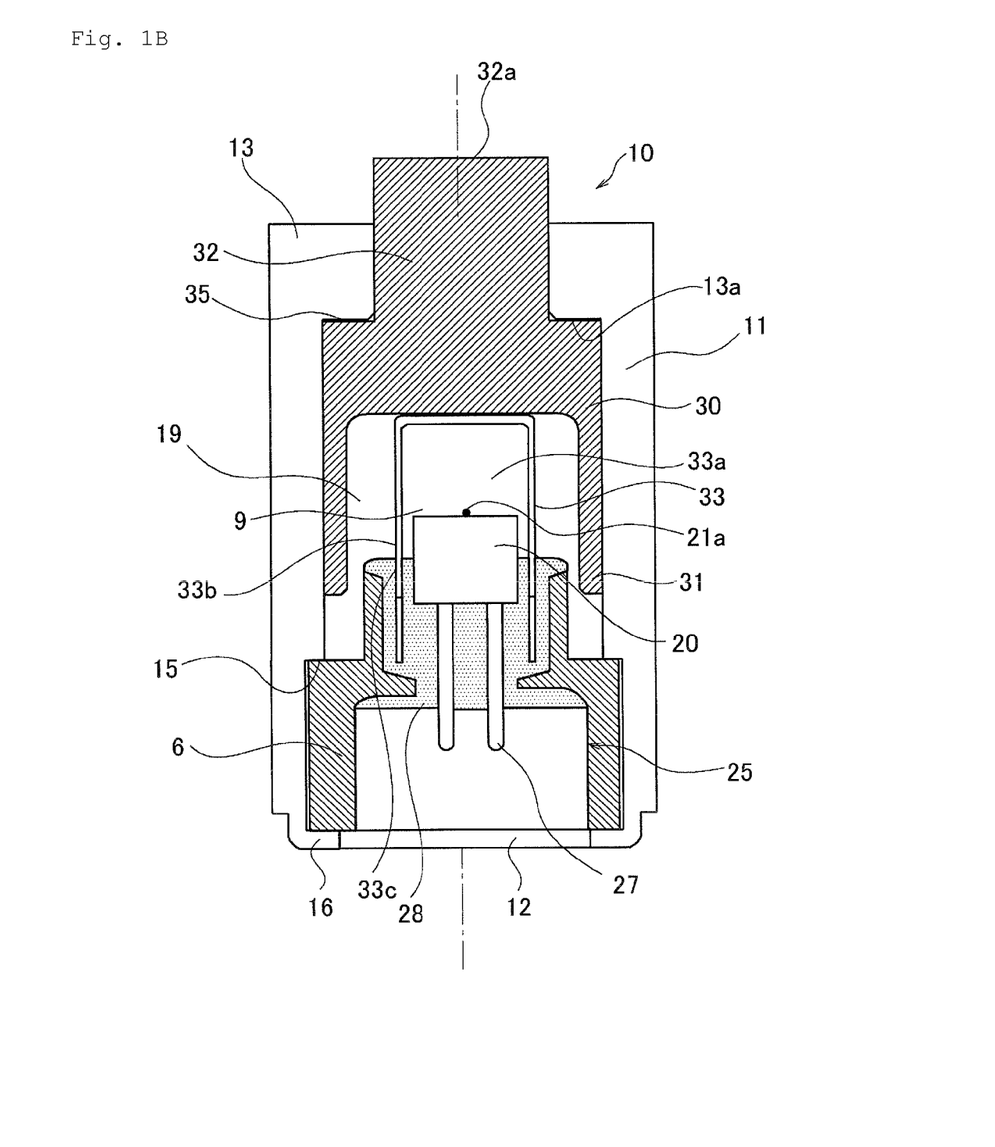
FIG. 1B shows a schematic structure of the pyrotechnic actuator mechanism according to the present disclosure, illustrating a structure brought about after the combustion of the ignition charge.
Figure 2:
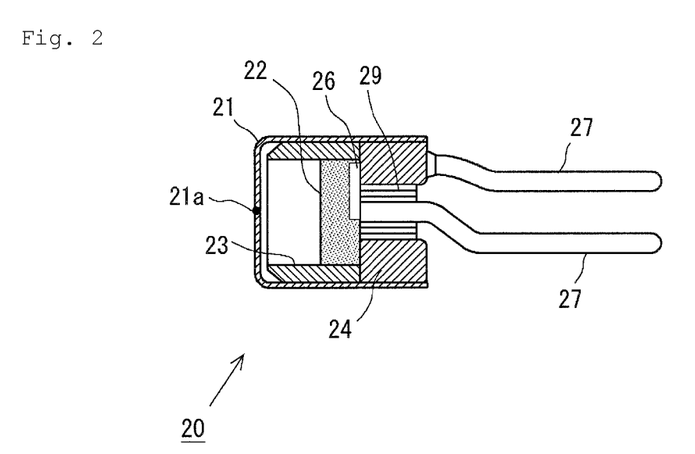
FIG. 2 shows a structure of an igniter included in the pyrotechnic actuator mechanism shown in FIGS. 1A and 1B.

FIG. 1A shows a schematic structure of a pyrotechnic actuator mechanism 10 according to the present disclosure (hereinafter simply referred to as "actuator mechanism"), illustrating a structure provided in a state before the combustion of an ignition charge, in a vertical cross section of the actuator mechanism 10. Further, FIG. 1B shows a schematic structure of the actuator mechanism 10 provided in a state after the combustion of the ignition charge, in a vertical cross section thereof. Further, FIG. 2 shows a schematic structure of an ignition unit 20 included in an igniter 25 of the actuator mechanism 10.

A housing 11 of the actuator mechanism 10 has a circular cross section. An electric ignition igniter 25 (hereinafter simply referred to as "igniter") is attached to an opening 12 disposed on one end side. The igniter 25 has an ignition unit 20 which includes the ignition charge. An example of the ignition unit 20 will now be explained on the basis of FIG. 2. In the ignition unit 20, the ignition charge 22 is combusted by means of the ignition current supplied from the outside. Specifically, a cup 21, the surface of which is covered with an insulating cover, defines, in the cup 21, a space for disposing the ignition charge 22. Then, a metal header 24 is arranged in the space, and the cup 21 is fixed to the metal header 24. Further, a cylindrical charge holder 23 is provided on an upper surface of the metal header 24. The ignition charge is held by the charge holder 23. A bridge wire 26, which electrically connects one conductive pin 27 and the metal header 24, is wired at the bottom portion of the ignition charge 22. Note that the two conductive pins 27 are fixed to the metal header 24 by the aid of an insulator 29 so that the two conductive pins 27 are mutually in the insulated state. Further, an open port of the cup 21, from which the two conductive pins 27 supported by the insulator 29 are allowed to extend outwardly, is protected by a mold portion 28 formed of a resin as shown in FIG. 1 in a state in which the insulation performance is satisfactorily maintained between the conductive pins 27. The mold portion 28 is formed by injection-molding a resin material in the production steps of producing the ignition unit 20.

In the ignition unit 20 configured in this way, when the voltage is applied between the two conductive pins 27 by an external power source, then the current flows through the bridge wire 26, and the ignition charge 22 is combusted thereby. In this situation, the combustion product, which is produced by the combustion of the ignition charge 22, is released from the opening of the charge holder 23 while breaking the cup 21. Note that an ignition unit 20, which has no charge holder 23, may be used in another method. In the case of the ignition unit 20 shown in FIG. 2, the portion, from which the combustion product is released, is the portion 21*a* disposed in the vicinity of the center of the top of the cup 21. In this arrangement, as shown in FIG. 1A, the space, which serves as the combustion chamber 9, is arranged in the vicinity of the portion 21*a*. The combustion chamber 9 is the closed space which is defined by a cover member 33 described later on, the ignition unit 20, and the mold portion 28. Therefore, the combustion product of the ignition charge 22 is sealed in the combustion chamber.

Note that the ignition charge 22 is preferably exemplified by a propellant containing zirconium and potassium perchlorate (ZPP), a propellant containing titanium hydride and potassium perchlorate (THPP), a propellant containing titanium and potassium perchlorate (TiPP), a propellant containing aluminum and potassium perchlorate (APP), a propellant containing aluminum and bismuth oxide (ABO), a propellant containing aluminum and molybdenum oxide (AMO), a propellant containing aluminum and copper oxide (ACO), a propellant containing aluminum and iron oxide (AFO), or a propellant composed of a combination of a plurality of the foregoing propellants. These propellants exhibit such characteristics that, although the propellants generate hot and high-pressure plasma during combustion immediately after ignition, when combustion products condense at a room temperature, the propellants do not contain gaseous components and the pressure generated decreases abruptly. It is also allowable that any propellant or pyrotechnic charge other than the above is used as the ignition charge, provided that the injection can be performed appropriately.

In this case, any additional ignition charge is not especially arranged in the combustion chamber 9. However, for example, a gas generating agent, which is combusted by the combustion product produced by the combustion of the ignition charge 22 to generate the gas, can be also arranged in the combustion chamber 9. As for an example of the gas generating agent, it is possible to exemplify a single base smokeless propellant including 98% by mass of nitrocellulose, 0.8% by mass of diphenylamine, and 1.2% by mass of potassium sulfate. Further, it is also possible to use various gas generating agents used for a gas generator for airbags and a gas generator for seat belt pretensioners. The combustion completion time can be changed for the gas generating agent by adjusting the dimension, the size, and the shape, especially the surface shape of the gas generating agent when the gas generating agent is arranged in the combustion chamber 9. Accordingly, the pressure transition in the combustion chamber 9 can be a desired transition.

Then, the igniter 25 is attached to one end side of the housing 11 in a state of being fixed to the igniter collar 6. Specifically, a caulking portion 16 is provided on one end side of the housing 11. A step portion of the igniter collar 6 is allowed to abut against an annular step portion 15 formed on the inner wall surface of the housing 11. In this state, the opposite end portion of the igniter collar 6 is caulked by the caulking portion 16 to effect the fixation with respect to the housing 11. Note that the igniter 25 including the ignition unit 20 is fixed to the igniter collar 6 by means of the mold portion 28.

Further, the cover member 33 is arranged so that the ignition unit 20 is covered therewith. In particular, the cover member 33 is arranged so that the portion 21*a* of the cup 21 of the ignition unit 20 (portion at which the combustion product of the ignition charge 22 is released) is covered therewith and the combustion chamber 9 as the closed space is formed between the cover member 33 and the ignition unit 20. Then, the cover member 33 is composed of a first wall member 33*a* which is a wall member having no through-hole or the like existing therethrough and which is arranged opposingly to the portion 21*a*, and a second wall member 33*b* which is a wall member having no through-hole or the like existing therethrough in the same manner as described above, which is connected to the circumference of the first wall member 33*a*, and which extends in the axial direction of the cover member 33. The extending direction of the second wall member 33*b* is the same as the propulsion direction of the piston 30 described later on. Further, a free end portion 33*c* of the second wall member 33*b*, which is disposed on a side opposite to a connecting end portion with respect to the first wall member 33*a*, is open. The free end portion 33*c* is embedded and temporarily fixed in the resin material of the mold portion 28. In this viewpoint, the mold portion 28 functions as the "fixing member" for the cover member 33. In the state of temporary fixation, the combustion chamber 9, which is defined by the cover member 33, the ignition unit 20, and the mold portion 28, has the hermetic sealing performance which is sufficiently secured or guaranteed.

In this arrangement, a protruding portion 13, which protrudes inwardly in the housing 11, is formed on a forward end side of the housing 11 (side of the upper end portion as viewed in FIG. 1A). An opening 14, which connects the inside and the outside of the housing, is formed at a central portion of the protruding portion 13. Further, an accommodating space 17, which is a columnar or cylindrical space and which accommodates the piston 30 made of metal therein, is formed in the housing 11. The accommodating space 17 is connected to the outside of the housing 11 via the opening 14. The piston 30 is formed integrally with a piston rod 32 which extends upwardly thereon. In a state shown in FIG. 1A, the piston rod 32 is inserted and fitted into the opening 14, and the piston 30 is inserted and fitted into the accommodating space 17. Then, the piston 30 and the piston rod 32 are movable in the axial direction in the housing 11, while maintaining a slidable state between the piston rod 32 and the opening 14 and a slidable state between the piston 30 and the accommodating space 17. For example, the outer diameter of the piston 30 is approximately the same as or approximately slightly smaller than the inner diameter of the accommodating space 17. The correlation between the inner diameter of the accommodating space 17 and the outer diameter of the piston 30 is adjusted so that the movement can be caused smoothly when the piston 30 is moved. Further, it is also appropriate that a lubricant is applied between the outer circumferential surface of the piston 30 and the inner wall surface of the accommodating space. Note that in the state shown in FIG. 1A, the forward end surface of the piston rod 32*a* (upper end surface as viewed in FIG. 1A) is flush with the outer surface of the protruding portion 13.

Further, the piston 30 has a cylindrical skirt portion 31 disposed at a lower portion. The inside of the skirt portion 31 forms an accommodating space 19 in which the ignition unit 20 of the igniter 25 is accommodated. In the state shown in FIG. 1A in which the igniter 25 is accommodated in the housing 11 by the aid of the igniter collar 6, the piston 30 and the piston rod 32 are positioned so that the first wall member 33a of the cover member 33 abuts against the lower surface of the piston 30 in the accommodating space 19.

In this arrangement, the distance (embedding distance) A, which is included in the length in the axial direction of the second wall member 33b of the cover member 33 and by which the cover member 33 is embedded in the mold portion 28, is set to be larger than the distance by which the piston 30 is movable in the accommodating space 17 of the housing 11, i.e., the distance B between an inner wall surface 13a of the protruding portion 13 and a shoulder portion 35 generated or formed by the difference in the outer diameter between the piston 30 and the piston rod 32 in the vicinity of the connecting portion between the piston 30 and piston rod 32. When the piston 30 is moved by the distance B, the movement thereof is regulated by the protruding portion 13. Therefore, the distance B is also the distance by which the piston 30 can be moved, and the distance B is also the distance by which the cover member 33 moved together with the piston 30 can be moved. In this arrangement, the position, at which the movement of the cover member 33 is regulated together with the piston 30, corresponds to the maximum propulsion position according to the present disclosure.

As for the embedding of the second wall member 33b in the mold portion 28, the fixing force (i.e., the relatively weak fixing force) is generated to such an extent that the cover member 33 is pushed in the propulsion direction by the pressure in the combustion chamber 9 generated when the ignition charge 22 is combusted in the ignition unit 20, the temporary fixed state between the second wall member 33b and the mold portion 28 is dissolved or canceled, and the cover member 33 becomes movable in the propulsion direction of the piston 30 so that the cover member 33 pushes the piston 30 upwardly. Therefore, when the ignition charge 22 is combusted, then the cover member 33 is moved in the upward direction as viewed in FIG. 1A, and the combustion chamber 9 is progressively expanded in the movement direction in accordance therewith. In this situation, the first wall member 33a pushes the lower surface of the piston 30 upwardly. Thus, as shown in FIG. 1B, the upper surface 32a of the piston rod 32 protrudes from the housing 11. In this way, the cover member 33 is arranged in the columnar form in the mold portion 28 so that the cover member 33 can be moved smoothly in accordance with the combustion of the ignition charge 22, and any projection and any protrusion/recess are not formed for the second wall member 33b. Therefore, the cover member 33 is temporarily fixed to the mold portion 28 in the temporary fixing state in which the cover member 33 is withdrawable relatively easily from the mold portion 28.

In this arrangement, as described above, the embedding distance A of the second wall member 32b is set to be longer than the movable distance of the cover member 33 (movable distance of the piston 30) B. Therefore, even when the piston 30 arrives at the maximally propelled position (maximum propulsion position), i.e., the position at which the shoulder portion 35 abuts against the inner wall surface 13a, then the free end portion 33c of the cover member 33 exists at the inside of the mold portion 28, and the cover member 33 is not disengaged from the mold portion 28. Therefore, when the piston 30 is driven and propelled by the combustion of the ignition charge 22 in the actuator mechanism 10, the hermetic sealing performance of the combustion chamber 9 is maintained until arrival at the state in which the piston 30 is maximally propelled. In this way, in the case of the actuator mechanism 10, the combustion energy can be efficiently transmitted to the piston 30 by the aid of the cover member 33 in the state in which the combustion product of the ignition charge 22 is sealed or enclosed in the combustion chamber 9. Note that the injection pressure of the resin, which is applied when the mold portion 28 is formed or molded, is preferably set to about 7 to 13 MPa in order to form the temporary fixing state for providing the hermetic sealing performance of the combustion chamber 9 and the efficient energy transmission as described above.

Note that the movement in the axial direction is prohibited in order that the piston 30 and the piston rod 32 do not protrude or jump out from the housing 11 before the combustion of the ignition charge 22. Specifically, the circumferential surface of the opening 14 is lightly caulked, and thus the jumping out of the piston rod 32 is prohibited. When the ignition charge 22 is combusted, the force, which is not less than the resistance force brought about by the caulking, is exerted.

As described above, in the actuator mechanism 10, the combustion product, which contains the residue or the like produced by the combustion of the ignition charge 22 in the ignition unit 20, is sealed in the combustion chamber 9 which is the closed space formed by the cover member 33, the ignition unit 20, and the mold portion 28. Therefore, the combustion product does not leak to the outside, and the combustion product does not flow out to the outside of the housing 11 as well. Further, the combustion energy, which is generated by the combustion of the ignition charge 22, is principally received by the first wall member 33a opposed to the portion 21a. Therefore, the combustion energy pushes the cover member 33 upwardly to efficiently drive and propel the piston 22. In this way, the actuator mechanism 10 makes it possible to establish both of the suppression of the discharge or emission of the residue produced by the combustion of the ignition charge 22 and the maintenance of the preferable output efficiency brought about by the actuator.

Second Embodiment

Figure 3A:
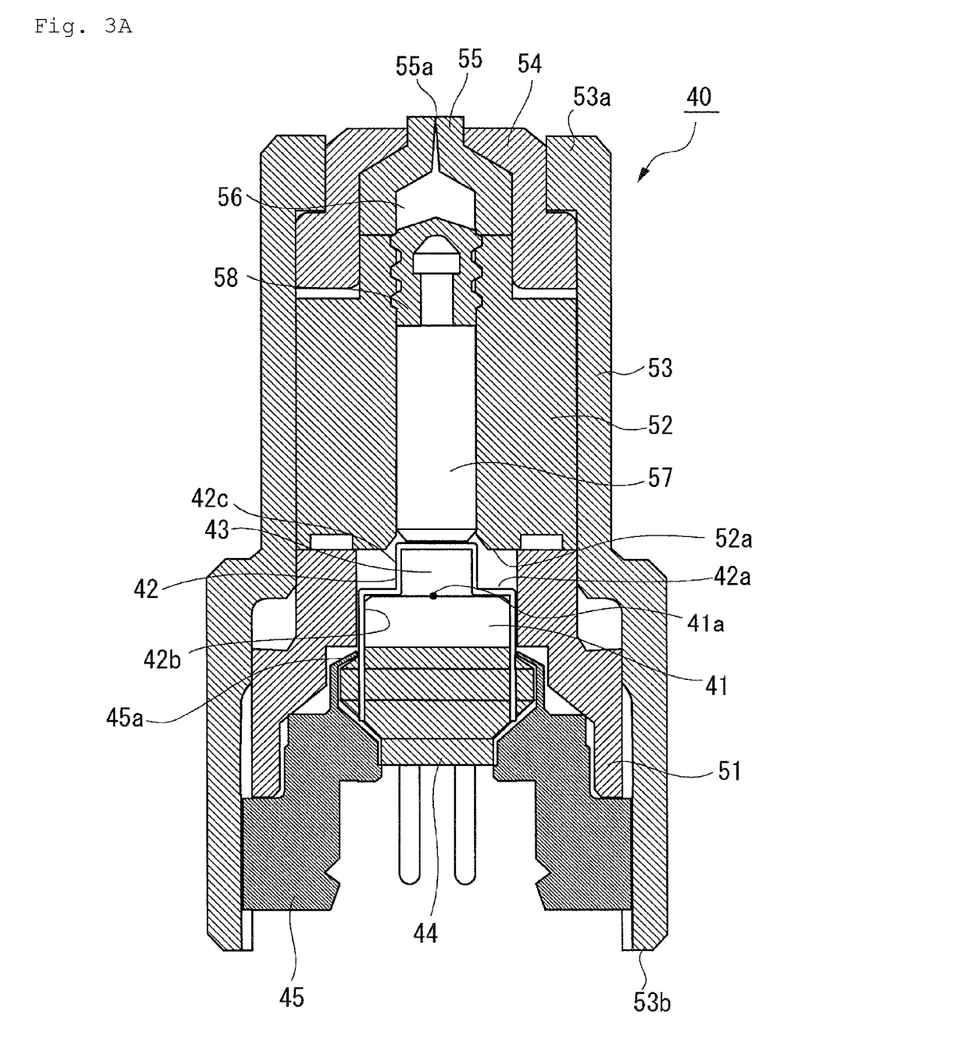
FIG. 3A shows a schematic structure of a syringe according to the present disclosure, illustrating a structure before the combustion of the ignition charge.
Figure 3B:
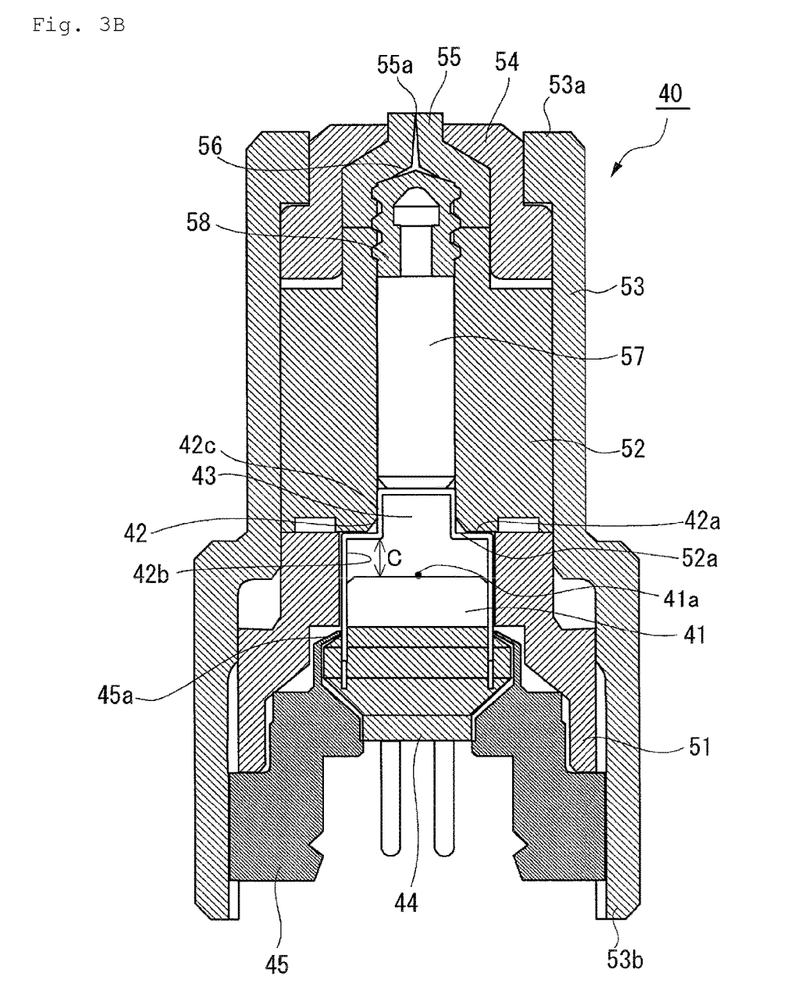
FIG. 3B shows a schematic structure of the syringe according to the present disclosure, illustrating a structure after the combustion of the ignition charge.

Next, an explanation will be made on the basis of FIGS. 3A and 3B about a syringe 40 which uses the pyrotechnic actuator mechanism according to the present disclosure (hereinafter simply referred to as "actuator mechanism" as well) as the driving source. The actuator mechanism has substantially the same operation principle as that of the actuator mechanism 10 described in the first embodiment. In this context, FIG. 3A shows a schematic structure of the syringe 40, illustrating a structure in a state before the combustion of the ignition charge in the actuator mechanism, in a vertical cross section of the syringe 40. Further, FIG. 3B shows a schematic structure of the syringe 40 in a state after the combustion of the ignition charge, in a vertical cross section thereof.

Note that in the following description of this specification, the injection objective substance, which is to be injected into an injection target area by the syringe 40, is generally referred to as "injection solution". However, this description includes no intention to limit the contents and the form of the substance to be injected. The component, which is to be delivered, for example, to a skin structure, may be either dissolved or not dissolved in the injection objective substance. Any specified form of the injection objective substance is available without any problem as well, for which various forms can be adopted, including, for example, liquid and gel form, provided that the injection objective substance can be discharged to the injection target area from a discharge hole 55a of a nozzle 55 by being pressurized.

The syringe 40 has a housing 53 which is formed to have a cylindrical shape. The housing 53 is provided with an electric ignition igniter for combusting the ignition charge and generating the energy in order to cause the discharge or injection. However, in FIGS. 3A and 3B, only the ignition unit 41, which is included in the electric ignition igniter, is depicted. Note that the ignition unit is substantially the same as the ignition unit 20 described in the first embodiment. Therefore, any detailed explanation of the ignition unit 41 will be omitted (see FIG. 2). Further, the syringe 40 is incorporated with a piston 57 which transmits the combustion energy brought about by the combustion of the ignition charge in the ignition unit 41 to the injection solution accommodated in an accommodating space 56.

In particular, the housing 53 is produced by the injection molding of the resin. As for the injection molding, it is possible to use any known method. As a resin material of the housing 53, for example, publicly-known nylon 6-12, polyarylate, polybutylene terephthalate, polyphenylene sulfide, or liquid crystal polymer can be used. A filler such as a glass fiber or a glass filler may be included in these kinds of resin 20 to 80 mass % of the glass fiber can be included in the polybutylene terephthalate. 20 to 80 mass % of the glass fiber can be included in the polyphenylene sulfide, 20 to 80 mass % of mineral can be included in the liquid crystal polymer.

In this arrangement, a protruding portion 53a, which protrudes in the inward direction of the housing 53, is formed on a forward end side of the housing 53 (side of the upper end portion as viewed in FIG. 3A). An opening is formed at a central portion of the protruding portion 53a. The inside and the outside of the housing 53 are connected to one another by the opening. Then, a first holder 54 is arranged at the inside of the housing 53 in a state in which the first holder 54 abuts against the protruding portion 53a. The first holder 54 retains a nozzle 55 at the inside thereof. Then, a second holder 52, which is arranged to press the nozzle 55 with respect to the first holder 54, is arranged at the inside of the housing 53. Note that the nozzle 55 and the second holder 52 may be formed in an integrated manner. A through-hole, which has a constant diameter in the axial direction, is formed at the inside of the second holder 52. One end of the through-hole is communicated with the space in which the ignition unit 41 is arranged, and the other remaining end arrives at the side of the accommodating space 56 for accommodating the injection solution in the nozzle 55.

Then, a piston 57 made of metal is arranged in the through-hole so that the piston 57 can be propelled in the axial direction in the through-hole. One end thereof is directed to the side of the space in which the ignition unit 41 is arranged. Further, the other remaining end is directed to the side of the accommodating space 56 for accommodating the injection solution. Note that a plunger 58 made of resin is provided on the forward end side of the piston 57. The space, which is formed between the plunger and the nozzle 55, is the accommodating space 56 in which the injection solution is accommodated. In this arrangement, the forward end portion of the plunger 58 has a shape which supplements or complements the shape of the accommodating space 56 on the side of the nozzle 55. That is, the shape of the outer surface of the forward end portion of the plunger 58 is approximately coincident with the shape of the accommodating space 56 on the side of the nozzle 55. Therefore, it is possible to maximally decrease the amount of the injection solution which is left in the accommodating space 56 upon the completion of the discharge or injection of the injection solution.

In this arrangement, for example, butyl rubber and silicon rubber can be adopted as the material for the plunger 58. Further, examples of the material include styrene-based elastomer, hydrogenated styrene-based elastomer, and the styrene-based elastomer and the hydrogenated styrene-based elastomer added with polyethylene, polypropylene, polybutene, polyolefin such as α-olefin copolymer, liquid paraffin, oil such as process oil, and powder inorganic matters such as talc, cast, and mica. Further, polyvinyl chloride-based elastomer, olefin-based elastomer, polyester-based elastomer, polyamide-based elastomer, and polyurethane-based elastomer, various rubber materials (in particular, those subjected to vulcanization) such as natural rubber, isoprene rubber, chloroprene rubber, nitrile-butadiene rubber, and styrene-butadiene rubber, mixtures of the kinds of elastomer and the kinds of rubber, and the like can be adopted as the material of the plunger. Further, the plunger 58 has a plurality of annular projections which are formed on the outer circumference of a columnar body. The projections are made of resin, and hence the projections are elastically deformed when the plunger 58 is inserted into the through-hole together with the piston 57. It is possible to enhance the degree of tight contact between the plunger 58 and the inner wall surface of the through-hole.

Further, a third holder 51 is arranged in the housing 58 so that the third holder 51 abuts against an end surface 52a of the second holder 52 on a side of the space in which the ignition unit 41 is arranged. Then, an igniter assembly, which is formed by caulking and fixing an intermediate assembly described later on including the ignition unit 41 with respect to the igniter collar 45, is retained by the third holder 51. In the igniter assembly, the ignition unit 41 is fixed to the mold portion 44 formed of the resin. Further, the cover member 42 is temporarily fixed to the mold portion 44 so that a release portion 41a of the cup of the ignition unit 41 for releasing the combustion product is covered therewith. Note that the mold portion 44 of this embodiment corresponds to the mold portion 28 of the first embodiment, any detailed explanation of which is omitted.

The cover member 42 will now be explained in detail. The cover member 42 is arranged so that the release portion 41a of the cup of the ignition unit 41 is covered therewith and the combustion chamber 43 as the closed space is formed between the cover member 42 and the ignition unit 41. Then, the cover member 42 is composed of a first wall member 42a which is a wall member having no through-hole or the like existing therethrough and which is arranged opposingly to the portion 41a, and a second wall member 42b which is a wall member having no through-hole or the like existing therethrough in the same manner as described above, which is connected to the circumference of the first wall member 42a, and which extends in the axial direction of the cover member 42. The second wall member 42b is arranged along the side surface of the ignition unit 41, and the extending direction thereof is the same as the propulsion direction of the piston 57. Further, a free end portion of the second wall member 42b, which is disposed on a side opposite to a connecting end portion with respect to the first wall member 42a, is open. The free end portion is embedded and temporarily fixed in the resin material of the mold portion 44. The temporary fixation is the same as or equivalent to that of the first embodiment. In the state of temporary fixation, the hermetic sealing performance is sufficiently secured or guaranteed for the combustion chamber 43 which is defined by the cover member 42 and the ignition unit 41.

Further, a columnar protruding portion 42c, which protrudes in the direction directed to the piston 57 from the first wall member 42a, is formed on the first wall member 42a of the cover member 42. The outer diameter of the protruding portion 42c is formed to be slightly smaller than the outer diameter of the piston 57, and the outer diameter of the first wall member 42a is formed to be larger than the outer diameter of the piston 57. Therefore, as shown in FIG. 3A, a step-shaped portion is formed on the cover member 42 in accordance with the difference between the outer diameter of the first wall member 42a and the outer diameter of the protruding portion 42c.

Then, the igniter assembly shown in FIG. 3A is formed by attaching the igniter collar 45 to the intermediate assembly in a state in which the ignition unit 41 is fixed to the mold portion 44 and the cover member 42 is temporarily fixed to the mold portion 44. The igniter collar 45 is provided with a caulking pawl 45a. At the beginning, the caulking pawl 45a is not bent. The intermediate assembly is inserted into the igniter collar 45 in this state. After that, the caulking pawl 45a is bent to caulk the intermediate assembly, and thus the igniter assembly shown in FIG. 3A is formed. In this way, the igniter assembly, which is formed by fixing the intermediate assembly including the ignition unit 41 to the igniter collar 45, is arranged in the housing 53 so that the igniter assembly abuts against the third holder 51. Further, the igniter assembly is fixed so that the igniter assembly is pressed against the third holder 51 at the end portion 53b of the housing 53 disposed on the side opposite to the protruding portion 53a. Note that a seal member, which includes, for example, an O-ring and a gasket, can be arranged at the respective abutment portions between the first holder 54 and the second holder 52, between the second holder 52 and the third holder 51, and between the third holder 51 and the igniter collar 45.

An explanation will be made about the operation of the syringe 40 constructed as described above. FIG. 3A shows the state brought about before the combustion of the ignition charge of the ignition unit 41. In this state, the top surface of the protruding portion 42c of the cover member 42 is brought in contact with the end surface of the piston 57 on the side opposite to the plunger 58. When the ignition current is supplied to the ignition charge to cause the combustion in this state, then the combustion product of the ignition charge flows from the portion 41a into the combustion chamber 43, and the pressure in the combustion chamber 43 is suddenly raised. In this situation, the cover member 42 is temporarily fixed to the mold portion 44. Therefore, the cover member 42 is moved upwardly as viewed in FIG. 3A in accordance with the increase in the pressure in the combustion chamber 43. The piston 57 is pushed upwardly toward the forward end side of the syringe 40, and the piston 57 is driven and propelled. Further, the combustion chamber 43 is progressively expanded in the propulsion direction of the piston 57. In this situation, the outer diameter of the protruding portion 42c of the cover member 42 is formed to be slightly smaller than the outer diameter of the piston 57. Therefore, when the piston 57 is pushed upwardly, the protruding portion 42c progressively enters the through-hole in the second holder 52. Then, as shown in FIG. 3B, when the first wall member 42a of the cover member 42 abuts against the end surface 52a of the second holder 52, the movement to push the piston 57 upwardly, which is caused by the cover member 42, is regulated. In this situation, the position, at which the movement of the cover member 42 is regulated, corresponds to the maximum propulsion position according to the present disclosure. In this way, the piston 57 is pushed upwardly in accordance with the movement of the cover member 42. Accordingly, the injection solution contained in the space 56 is pressurized, and the injection solution is discharged or injected from the discharge hole 55a of the nozzle 55 toward the injection target area.

Further, the embedding distance of the second wall member 42b in the mold portion 44 is also set to be longer than the movable distance of the cover member 42 and the piston 57, in the same manner as in the first embodiment. The movable distance of the cover member 42 and the like in this embodiment is the distance between the first wall member 42a of the cover member 42 and the end surface 52a of the second holder 52 for regulating the movement of the cover member 42, which corresponds to the distance C shown in FIG. 3B. In this way, the correlation is retained between the embedding distance and the movable distance, and thus the free end portion of the second wall member 42b exists in the mold portion 44 during the period of movement of the cover member 42, in the same manner as in the first embodiment. Therefore, the combustion product of the ignition charge is continuously sealed in the combustion chamber 43. Therefore, it is possible to efficiently realize the transmission of the combustion energy to the piston 57 by the aid of the cover member 42, while sufficiently suppressing the discharge or emission of the residue contained in the combustion product to the outside.

Third Embodiment

Next, an igniter assembly 60 according to the present disclosure will be explained on the basis of FIG. 4. The igniter assembly 60 is an assembly which is incorporated into the pyrotechnic actuator mechanism according to the present disclosure and which includes an ignition unit to cause the combustion of the ignition charge. The ignition unit 61, which is included in the igniter assembly 60, is substantially the same as the ignition unit 20 described in the first embodiment and the ignition unit 41 described in the second embodiment, any detailed explanation of which is omitted (see FIG. 2). Then, in the igniter assembly 60, the ignition unit 61 is fixed to a mold portion 64 formed of resin. Further, a cover member 62 is temporarily fixed to the mold portion 64 so that the release portion of the cup of the ignition unit 61 for releasing the combustion product is covered therewith. Note that the mold portion 64 of this embodiment corresponds to the mold portion 28 of the first embodiment and the mold portion 44 of the second embodiment, any detailed explanation of which is omitted. The mold portion 64 is provided in order to fix the ignition unit 61 to an igniter collar 70. Note that a projection 73 is provided at a portion of an inner wall surface of the igniter collar 70 at which the mold portion 64 is formed so that the position is not changed after the mold portion 64 is formed at the inside of the igniter collar 70.

Figure 4:
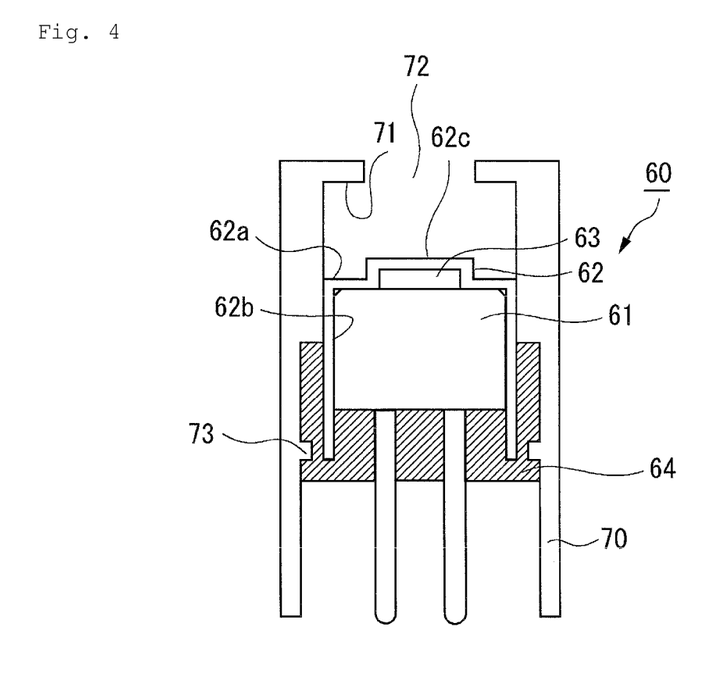
FIG. 4 shows a schematic structure of a first igniter assembly according to the present disclosure.

Further, a protrusion 71, which protrudes on the inner side of the igniter collar 70, is formed at the forward end side of the igniter collar 70 (side of the upper end portion as viewed in FIG. 4). An opening 72 is positioned at the center of the protrusion 71. For example, a piston (not shown), to which the combustion energy brought about by the combustion of the ignition charge in the ignition unit 61 is transmitted, is arranged in the opening 72. That is, the opening 72 forms a part or all of the space in which the piston or the like is driven and propelled.

The cover member 62 will now be explained in detail. The cover member 62 is arranged so that the portion of the cup of the ignition unit 61, from which the combustion product of the ignition charge is released, is covered therewith, and a combustion chamber 63, which is a closed space, is formed between the cover member 62 and the ignition unit 61. Then, the cover member 62 is composed of a first wall member 62a which is a wall member having no through-hole or the like existing therethrough and which is arranged opposingly to the release portion, and a second wall member 62b which is a wall member having no through-hole or the like existing therethrough in the same manner as described above, which is connected to the circumference of the first wall member 62a, and which extends in the axial direction of the cover member 62. The second wall member 62b is arranged along the side surface of the ignition unit 61, and the extending direction thereof is the same as the output direction brought about by the igniter assembly 60. Further, a free end portion of the second wall member 62b, which is disposed on a side opposite to a connecting end portion with respect to the first wall member 62a, is open. The free end portion is embedded and temporarily fixed in the resin material of the mold portion 64. The temporary fixation is the same as or equivalent to those of the first embodiment and the second embodiment. In the state of temporary fixation, the hermetic sealing performance is sufficiently secured or guaranteed for the combustion chamber 63 which is defined by the cover member 62 and the ignition unit 61.

Further, a columnar protruding portion 62c, which protrudes in the direction directed to the opening 72 from the first wall member 62a, is formed on the first wall member 62a of the cover member 62. The outer diameter of the protruding portion 62c is formed to be slightly smaller than the inner diameter of the opening 72, and the height of the protruding portion 62c is approximately the same as the thickness of the protruding portion 71. Therefore, when the cover member 62 is moved upwardly as described later on, and the movement is regulated by the abutment against the inner surface of the protruding portion 71, then the protruding portion 62c is fitted into the opening 72, and the top surface of the protruding portion 62c is approximately flush with the outer surface of the protruding portion 71.

An explanation will be made about the operation of the igniter assembly 60 constructed as described above. When the ignition current is supplied to the ignition charge of the ignition unit 61 to cause the combustion, then the combustion product of the ignition charge flows into the combustion chamber 63, and the pressure in the combustion chamber 63 is suddenly raised. In this situation, the cover member 62 is temporarily fixed to the mold portion 64. Therefore, the cover member 62 is moved upwardly as viewed in FIG. 4 in accordance with the increase in the pressure in the combustion chamber 63. Then, when the first wall member 62a of the cover member 62 abuts against the inner surface of the protruding portion 71, the movement of the cover member 62 is regulated. In this arrangement, the position, at which the movement of the cover member 62 is regulated, corresponds to the maximum propulsion position according to the present disclosure. In this way, the piston is pushed upwardly in accordance with the movement of the cover member 62. Accordingly, the combustion energy of the ignition charge in the igniter assembly 60 can be efficiently converted into the propulsion force of the piston.

Further, the embedding distance of the second wall member 62b in the mold portion 64 is also set to be longer than the movable distance of the cover member 62, in the same manner as in the first embodiment and the second embodiment. The movable distance of the cover member 62 in this embodiment is the distance between the first wall member 62a of the cover member 62 and the inner surface of the protruding portion 71 for regulating the movement of the cover member 62. In this way, the correlation is retained between the embedding distance and the movable distance, and thus the free end portion of the second wall member 62b exists in the mold portion 64 during the period of movement of the cover member 62, in the same manner as in the first embodiment and the second embodiment. Therefore, the combustion product of the ignition charge is continuously sealed in the combustion chamber 63. Therefore, it is possible to efficiently realize the transmission of the combustion energy by the aid of the cover member 62, while sufficiently suppressing the discharge of the residue contained in the combustion product to the outside.

Modified Embodiment

Figure 5:
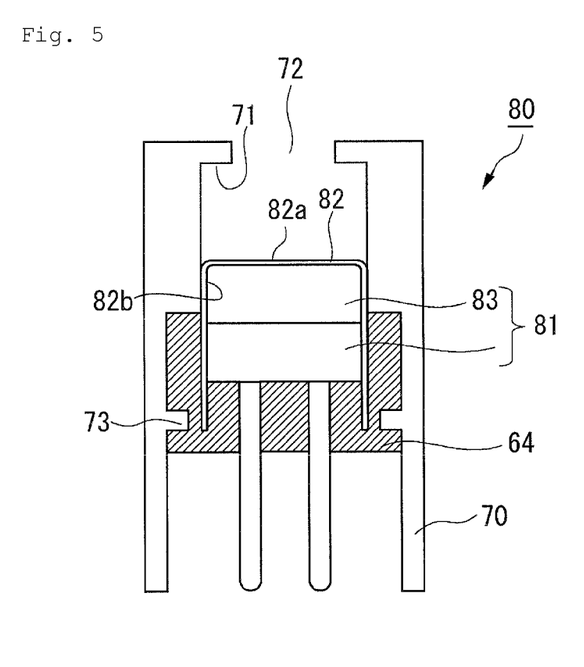
FIG. 5 shows a schematic structure of a second igniter assembly according to the present disclosure.

In this section, FIG. 5 shows a modified embodiment of the igniter assembly according to the present disclosure. The igniter assembly according to the modified embodiment is referred to by reference numeral 80. Note that the components or parts of the igniter assembly 80 according to the modified embodiment, which are common to those of the igniter assembly 60 according to the embodiment described above, are designated by the same reference numerals, any detailed explanation of which is omitted thereby. Specifically, the igniter collar 70 of the igniter assembly 80 and the components or parts relevant thereto (protruding portion 71, opening 72, projection 73) are the same as those of the igniter assembly 60. Further, the mold portion 64, which is provided to fix the ignition unit 81 to the igniter collar 70 as described later on, is also common to the igniter assemblies 80, 60.

In this arrangement, the ignition unit 81, which is provided for the igniter assembly 80, has the ignition charge disposed at the inside thereof, in the same manner as the embodiment described above. The ignition current is supplied from the conductive pin, and thus the combustion of the ignition charge is caused. In this arrangement, the ignition unit 81 does not have the cup 21 which is possessed, for example, by the ignition unit 20 according to the embodiment described above. A cover member 82 is provided in place of the cup 21. Accordingly, the space for accommodating the ignition charge is formed in the ignition unit 81. As described above, a part of the cup 21 is destroyed by the combustion of the ignition charge, and the combustion product of the ignition charge is released from the destroyed portion. That is, the cup 21 also defines the release portion for releasing the combustion product in relation to the ignition unit 20 or the like. On the other hand, the cover member 81 has a first wall member 82a which is a wall member having no through-hole or the like existing therethrough and which forms the top surface, and a second wall member 82b which is a wall member having no through-hole or the like existing therethrough in the same manner as described above, which is connected to the circumference of the first wall member 82a, and which extends in the axial direction of the cover member 82. The both wall members have strengths to such an extent that the wall members are not destroyed by the pressure generated by the combustion of the ignition charge.

Then, in the igniter assembly 80, the space, which is surrounded by the cover member 82, is filled with the ignition charge. Further, the first wall member 82*a* is arranged opposingly to the charge holder (not shown in FIG. 5, see FIG. 2) in which the ignition charge of the ignition unit 81 is placed. In this arrangement, the second wall member 82*b* is arranged therearound. The cup does not exist, and hence the combustion product of the ignition charge is diffused radially in the cover member. Then, the cover member 82 covers the release portion by means of the first wall member 82*a* and the second wall member 82*b*. Therefore, the internal space, which is formed by being covered with the cover member 82, is the combustion chamber 83 of the ignition unit 81.

Further, the free end portion of the second wall member 82*b*, which is disposed on a side opposite to the connecting end portion with respect to the first wall member 82*a*, is embedded and temporarily fixed in the resin material of the mold portion 64. The temporary fixation is the same as or equivalent to that of the third embodiment described above. Note that the second wall member 82*b* is not fixed to any specified portion of the ignition unit 81, for example, an unillustrated metal header 24. The second wall member 82*b* is merely temporarily fixed to the mold portion 64. Therefore, the movement of the cover member 82, which is directed toward the opening 72, is not inhibited when the ignition charge is combusted in the ignition unit 81.

Further, the embedding distance of the second wall member 82*b* embedded in the mold portion 64 is also set to be longer than the movable distance of the cover member 82, in the same manner as in the third embodiment described above. In this modified embodiment, the movable distance of the cover member 82 is the distance between the first wall member 82*a* of the cover member 82 and the inner surface of the protruding portion 71 which regulates the movement of the cover member 82. In this way, the correlation is retained between the embedding distance and the movable distance, and thus the free end portion of the second wall member 82*b* exists in the mold portion 64 during the period of movement of the cover member 82, in the same manner as in the third embodiment described above. Therefore, the combustion product of the ignition charge is continuously sealed in the combustion chamber 83.

As described above, it is possible to efficiently realize the transmission of the combustion energy to the outside by the aid of the cover member 82, while sufficiently suppressing the discharge of the residue contained in the combustion product to the outside, in the same manner as in the third embodiment described above, although the cup of the ignition unit 81 is omitted to decrease the number of parts in the igniter assembly 80.

The invention claimed is:

1. A pyrotechnic actuator mechanism which has an ignition unit including an ignition charge to be ignited by an ignition current supplied from outside and which includes a piston constructed to be driven and propelled in a propulsion hole provided in a housing in accordance with combustion energy of the ignition charge, the pyrotechnic actuator mechanism comprising:
   a cover member which covers a predetermined portion of the ignition unit including at least a release portion for releasing, from the ignition unit, a combustion product produced by combustion of the ignition charge in the ignition unit, which is formed to define a predetermined closed space between the cover member and the ignition unit, and which is arranged to transmit the combustion energy of the ignition charge to the piston; and
   a fixing member which fixes the ignition unit before and after the combustion of the ignition charge, wherein the cover member includes:
   a first wall member which is a wall member for defining the predetermined closed space, which is opposed to the predetermined portion of the ignition unit, and which is brought in contact with the piston; and
   a second wall member which is a wall member connected to the first wall member, for defining the predetermined closed space, which extends in the propulsion direction of the piston, and which has a free end portion disposed on a side opposite to a connecting end portion with respect to the first wall member, the free end portion being embedded in the fixing member, and wherein:
   the cover member is moved in the propulsion direction so that the predetermined closed space is expanded in the propulsion direction of the piston when the ignition charge is combusted, and the movement of the cover member in the propulsion direction is regulated so that a state, in which the free end portion of the second wall member is embedded in the fixing member, is maintained at a maximum propulsion position of the cover member.

2. The pyrotechnic actuator mechanism according to claim 1, wherein an embedded state of the free end portion in the fixing member is maintained by means of such an arrangement that an embedding distance of the second wall member in the fixing member in an uncombusted state of the ignition charge is longer than a movement distance of the cover member in the propulsion direction at a maximum propulsion position of the cover member.

3. The pyrotechnic actuator mechanism according to claim 1, wherein:
   the cover member further includes a protruding portion which is disposed at a portion of contact with the piston at the first wall member and which protrudes toward the piston; and
   an outer diameter of the protruding portion is formed to be smaller than an outer diameter of the piston, and an outer diameter of the first wall member is formed to be larger than the outer diameter of the piston.

4. The pyrotechnic actuator mechanism according to claim 3, wherein the cover member arrives at the maximum propulsion position by bringing the first wall member in contact with an end surface of the housing provided with the propulsion hole and regulating the movement of the cover member in the propulsion direction.

5. The pyrotechnic actuator mechanism according to claim 3, wherein a gas generating agent, which is combusted by a combustion product of the ignition charge to generate a gas, is arranged in the protruding portion.

6. The pyrotechnic actuator mechanism according to claim 1, wherein:
   the fixing member includes a mold portion which is formed of a resin material and which fixes the ignition unit;
   the cover member is temporarily fixed by the mold portion in a state in which the first wall member is not embedded in the mold portion and in a state in which a wall surface of the second wall member including the free end portion is embedded in the mold portion; and
   the mold portion fixes the ignition unit with respect to an inner wall surface of the housing.

7. The pyrotechnic actuator mechanism according to claim 6, wherein the second wall member is embedded in the mold portion so that the second wall member is in a straight column state along with the propulsion direction in the mold portion.

8. The pyrotechnic actuator mechanism according to claim 1, wherein the first wall member and the piston are arranged in a contact state in a state in which the ignition charge is not combusted.

9. A syringe comprising:
the pyrotechnic actuator mechanism as defined in claim 1;
an enclosure in which an injection objective substance to be injected into an injection target area is enclosed; and
a nozzle unit which has a flow passage for discharging the pressurized injection objective substance into the injection target area, the injection objective substance enclosed in the enclosure being pressurized by the aid of the piston driven and propelled by the combustion of the ignition charge in the pyrotechnic actuator.

10. An igniter assembly comprising:
an electric ignition igniter which has an ignition unit including an ignition charge;
an igniter collar which accommodates the electric ignition igniter;
a cover member which covers a predetermined portion of the ignition unit including at least a release portion for releasing, from the ignition unit, a combustion product produced by combustion of the ignition charge in the ignition unit, which is formed to define a predetermined closed space between the cover member and the ignition unit, and which outputs combustion energy of the ignition charge in a predetermined output direction; and
a fixing member which fixes the electric ignition igniter to the igniter collar before and after the combustion of the ignition charge, wherein the cover member includes:
a first wall member which is a wall member for defining the predetermined closed space and which is opposed to the predetermined portion of the ignition unit; and
a second wall member which is a wall member connected to the first wall member, for defining the predetermined closed space, which extends in the predetermined output direction, and which has a free end portion disposed on a side opposite to a connecting end portion with respect to the first wall member, the free end portion being embedded in the fixing member, and wherein:
the cover member is moved in the predetermined output direction so that the predetermined closed space is expanded in the predetermined output direction when the ignition charge is combusted, and the movement of the cover member in the predetermined output direction is regulated so that a state, in which the free end portion of the second wall member is embedded in the fixing member, is maintained at a maximum propulsion position of the cover member.

11. The igniter assembly according to claim 10, wherein an embedded state of the free end portion in the fixing member is maintained by means of such an arrangement that an embedding distance of the second wall member in the fixing member in an uncombusted state of the ignition charge is longer than a movement distance of the cover member in the predetermined output direction at a maximum propulsion position of the cover member.

12. The igniter assembly according to claim 10, wherein:
the igniter collar has a stopper member with which the cover member is brought in contact when the cover member is moved in the predetermined output direction in an igniter accommodating space for accommodating the electric ignition igniter; and
when the ignition charge is combusted and the cover member is moved in the predetermined output direction, then the first wall member is brought in contact with the stopper member, the movement of the cover member in the predetermined output direction is regulated, and thus the cover member arrives at the maximum propulsion position.

13. The igniter assembly according to claim 10, wherein:
the fixing member includes a mold portion which is formed of a resin material and which fixes the electric ignition igniter to the igniter collar; and
the cover member is temporarily fixed by the mold portion in a state in which the first wall member is not embedded in the mold portion and in a state in which a wall surface of the second wall member including the free end portion is embedded in the mold portion.

14. The igniter assembly according to claim 10, wherein:
the electric ignition igniter has a header portion which retains the ignition charge; and
the cover member forms, on the header portion, an ignition charge accommodating space for accommodating the ignition charge together with the header portion in a state in which the cover member is not fixed to the header portion.

15. The igniter assembly according to claim 10, wherein a gas generating agent, which is combusted by a combustion product to generate a gas, is arranged at a position disposed in the cover member at which the combustion product of the ignition charge can be brought in contact therewith.

* * * * *